United States Patent [19]

Carlson et al.

[11] Patent Number: 5,370,783
[45] Date of Patent: Dec. 6, 1994

[54] ELECTRODE

[75] Inventors: William P. Carlson, Hoffman Estates, Ill.; James B. Bushman, Medina, Ohio

[73] Assignee: Corrpro Companies, Inc., Medina, Ohio

[21] Appl. No.: 739,193

[22] Filed: Aug. 1, 1991

[51] Int. Cl.⁵ .................. G01N 27/31; G01N 27/401; C23F 13/00
[52] U.S. Cl. ....................... 204/435; 204/196; 204/197
[58] Field of Search ............. 204/147, 148, 196, 197, 204/435

[56] References Cited

U.S. PATENT DOCUMENTS

| | | | |
|---|---|---|---|
| 2,360,244 | 10/1944 | McAnneny | 204/196 |
| 2,567,855 | 9/1951 | Pippin et al. | 204/197 |
| 3,145,158 | 8/1964 | Matsuyama | 204/435 |
| 3,192,144 | 6/1965 | Heuze | 204/435 |
| 3,424,664 | 1/1969 | Severinghaus | 204/435 |
| 3,438,875 | 4/1969 | Watanabe et al. | 204/435 |
| 3,461,051 | 8/1969 | Vrable | 204/196 |
| 3,787,307 | 1/1974 | Schwab et al. | 204/435 |
| 4,166,021 | 8/1979 | Ross et al. | 204/435 |

*Primary Examiner*—T. Tung
*Attorney, Agent, or Firm*—Renner, Otto, Boisselle & Sklar

[57] ABSTRACT

An electrode is disclosed which is particularly useful as a reference electrode in cathodic protection systems. In any reference electrode or half cell, its continued stability is predominantly dependent on the metal ion concentration around it. In time such ions tend to leach away reducing the stability, effectiveness and life of the electrode. With the present invention such ions in the electrolyte may be replenished by the addition of a concentrated solution of metal salt to a ceramic canister which may include a glaze coating which may have one or more diffusion ports permitting the metal salt solution to leach at a controlled slow rate to the area surrounding the electrode ensuring continued stability and longer effective life for the electrode. The one or more diffusion ports also provide a low resistance current path to or from the lead within to the canister and the surrounding electrolyte.

12 Claims, 2 Drawing Sheets

ELECTRODE

This invention relates generally as indicated to an electrode for use in cathodic protection systems and more particularly to a reference electrode useful in connection with cathodic protection systems.

BACKGROUND OF THE INVENTION

Cathodic protection systems are widely used to protect for example buried metal structures or steel in reinforced concrete. Two types of systems are usually employed; those using gavanic anodes, and those using impressed current anodes. In either case, reference electrodes are widely used in cathodic protection systems to maintain and monitor the system at precise protective potential levels. Reference electrodes are often connected to electronic control systems which monitor and maintain cathodic protection systems on a continuing basis. Readings obtained from a reference electrode are, however, only as reliable as the reference electrode itself.

Underground or underwater reference electrodes of the copper-copper sulfate or silver-silver chloride type have been developed for use with cathodic protection systems and are widely used. An example of such reference electrodes or cells are those sold by Harco Corporation of Medina, Ohio under the trademark PERMACELL®. Such underground cells consist essentially of a relatively elongated plastic tube equipped with a special ion trap or wooden plug at the end of the cell to prevent contamination of the cell by the surrounding electrolyte. The tube contains a plaster/copper sulfate mix. The cell is then prepackaged in a special backfill to ensure both low contact resistance and long term stability.

Since the materials react differently, there are numerous problems in the fabrication, storage or shelf life, and long-term life. All the components must interact in order for the cell to last. If it freezes, it no longer will operate. If it dries out, it stops working. Fabricating the cell is labor intense and requires some type of controlled environment. The assembly procedure must be strictly adhered to throughout fabrication. Cells cannot be recharged if anything should fail, or, if one thinks it has failed, it cannot be verified.

In a typical system one or more of the reference cells may be installed at various locations in, around or beneath a structure being protected and connected either in parallel to provide an average potential reading or into a rotary switch, for example, enabling the operator to select any one of the reference cells as a signal source for the automatic system. Such cells have a design life of approximately fifteen years.

To replace such a cell in an inaccessible location can be much more expensive than the cell itself. This is especially true if the cell or electrode is buried under the structure of concern or is utilized in a reinforced concrete structure such as bridge decks, piers, pavement, garages, etc., of both the poured-in-place and precast type.

Also, such cells usually only have a single lead and thus it is difficult if not impossible to test the cell for accuracy or stability. Also, the environment of a structure being protected can become quite dry and in such dry environments the resistance between the cell and the surrounding electrolyte increases. Moreover, in any half cell or electrode its stability is fundamentally dependent on the metal ion concentration around it. Such ions tend to leach away and this is particularly true in extremely dry environments.

SUMMARY OF THE INVENTION

An electrode using a ceramic or earthenware slightly porous canister is provided which is particularly useful as a reference electrode in cathodic protection systems. In any reference electrode or half cell, its continued stability is predominantly dependent on the metal ion concentration around it. In time such ions tend to leach away reducing the stability, effectiveness and life of the electrode. With the present invention a salt solution leaches through the canister at a controlled slow rate and such ions in the contained electrolyte may be replenished. The canister may be provided with a glaze coating which may have one or more diffusion ports permitting the metal salt solution to leach at a controlled slow rate to the area surrounding the electrode. The one or more diffusion ports also provide a low resistance current path to or from the lead within to the canister and the surrounding electrolyte. A tube leading to the canister permits the salt solution to be replenished and also may provide an electrical measurement path for calibration. The tube when filled may then acts like a salt bridge to provide remote sensing or testing of the cell to determine its continued stability, quite apart from the system or controls to which the electrode is connected. By the use of the tube, a portable reference electrode may be utilized at the supply to determine the authenticity, stability and accuracy of the electrode during its service life.

It is an object of the present invention to provide a reference cell of simple construction using non-degrading materials such as ceramics. It is also important to provide a cell which does not employ porous plugs, etc., to provide electric contact to the environment, nor use different materials affected by coefficients of expansion.

The ceramic canister may have one or more diffusion ports. The diffusion rate through the ceramic canister is controllable through glazing techniques and diffusion port location. This provides a cell where the life is controllable and determinable. The cell is rechargeable and shelf life is indefinite. The cell is not affected by climatic changes, and provides uniform reproducible results.

Reduced size of the canister requires less moisture to maintain cell stability. The cell can be calibrated without excavation, and can be charged just prior to installation.

Other objects and advantages of the present invention will become apparent as the following description proceeds.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION OF THE PREFERRED EMBODIMENTS

Figure 1:
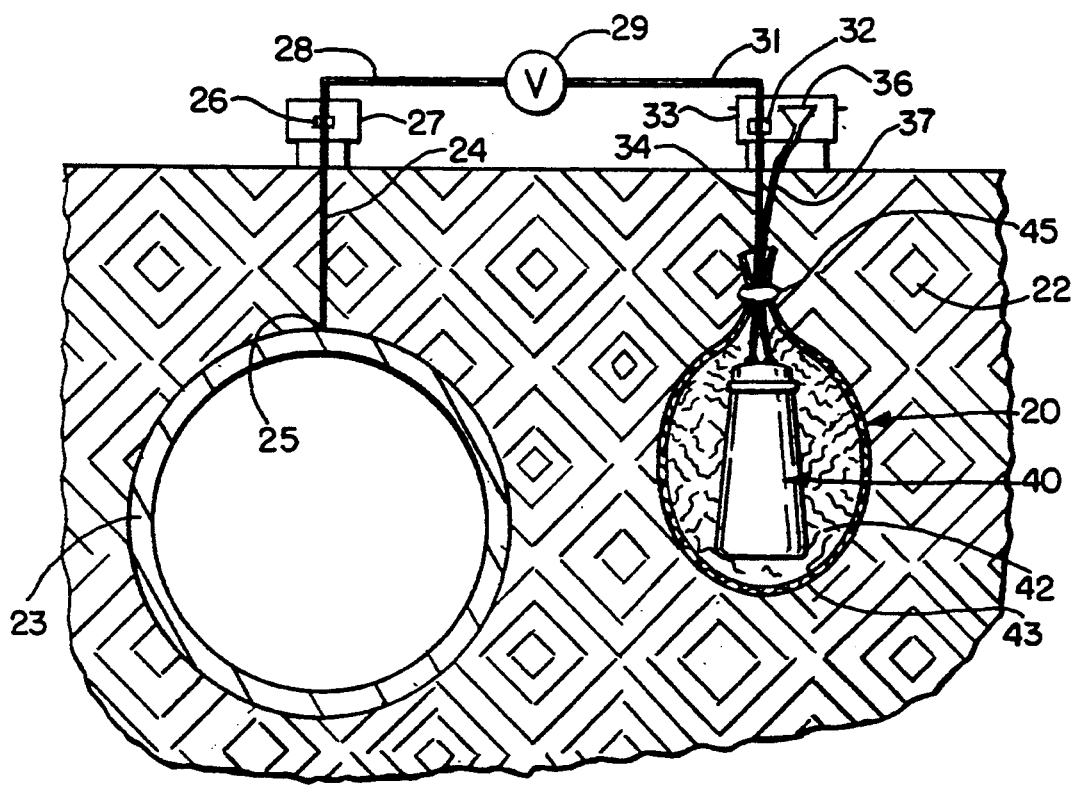
FIG. 1 is a schematic not to scale section of a reference electrode in accordance with the present invention positioned appropriately from a cathodically protected buried structure electrically connected thereto through a voltmeter.
Figure 2:
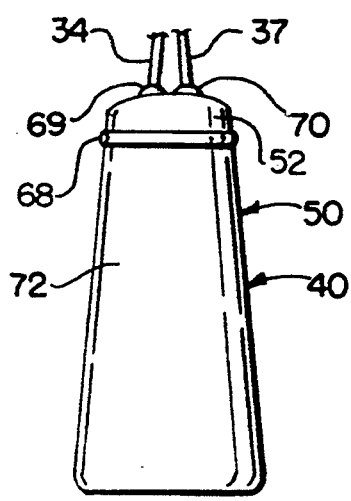
FIG. 2 is a side elevation of the ceramic canister of the present invention.
Figure 3:
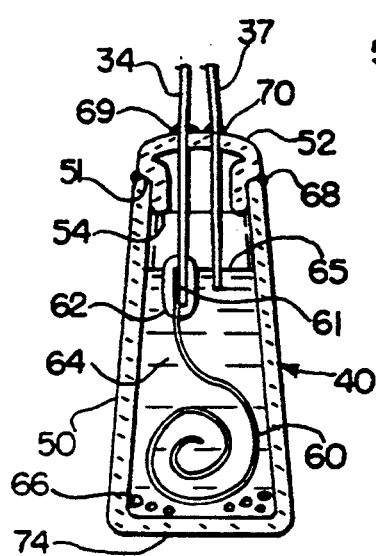
FIG. 3 is a vertical section through the ceramic canister.
Figure 4:
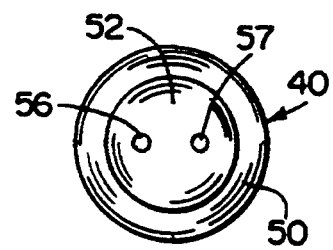
FIG. 4 is a top plan view of the canister.

Referring initially to FIG. 1 there is illustrated a reference cell 20 in accordance with the present invention buried in an electrolyte such as soil 22 at an appropriate distance from an underground metal structure such as pipeline 23. A lead 24 is connected to the pipe at 25. The lead 24 extends to connection 26 in test station 27. One lead 28 of voltmeter 29 may be connected at 26 while the other lead 31 is connected at 32 in test station 33 to lead 34 extending downwardly from the test station to the reference electrode 20. Both test stations 27 and 33 may have removable caps or plates to provide access to the interior or to the connections. However the test station 33 also includes a funnel 36, to the spout of which is connected plastic tube 37 which leads to ceramic canister 40.

As indicated, FIG. 1 is not to scale. The canister 40 may be approximately two to three inches in height and is surrounded by a hygroscopic mixture 42 contained in a cloth bag 43. It will of course be appreciated that the diameter of the pipe 23 being protected may vary substantially being several feet or more in diameter and also buried to a substantial depth.

The hygroscopic mixture may for example comprise approximately 75% bentonite or Wyoming clay, 20% gypsum, and 5% copper-copper sulfate. The backfill is a hygroscopic material designed to hold moisture and also act as a filter to keep bad or unwanted ions away from the electrode, while also keeping the good or wanted ions at the surface of the canister. The cloth sack filled with the hygroscopic material is simply tied around the top as indicated at 45 with beth the lead and the plastic tube extending through the tied top.

Referring now to FIGS. 2-6 in addition to FIG. 1, it will be seen that the canister 40 includes a main body 50 with slightly inwardly tapering conical side walls 50. The main portion or vessel of the canister terminates in top rim 51 and a ceramic cap or closure 52 seats on top of the rim 51 and includes a cylindrical skirt 54 which telescopes within the top rim 51 of the main body of the canister. The cap is provided with two holes indicated at 56 and 57 accommodating the lead 34 and the plastic tube 37.

Wire 34 may be a No. 14 AWG insulated wire which is connected to a coiled copper core 60 through soldered connection 61 which may be encased in a heat shrink encapsulation 62. The tube 37 may be simply a quarter inch plastic tube which extends down through the cap and into the top of the main body of the canister.

In use the main body of the canister is filled with a saturated copper sulfate $CuSO_4$ solution indicated generally at 64 to the level of about 70% of its capacity seen at 65. Additional undissolved copper sulfate crystals 66 are also generally provided that can dissolve in the solution as the previously dissolved ions slowly leach out of the canister. This action maintains the concentration of the solution and therefore the stability of the cell. Also in use, the cap is peripherally sealed at the top rim of the main vessel 50 of the canister as seen at 68 while both the lead wire and the plastic tube are sealed through the top of the cap as seen at 69 and 70, respectively. A suitable quick setting instant adhesive may be used to form the seal.

Figure 5:
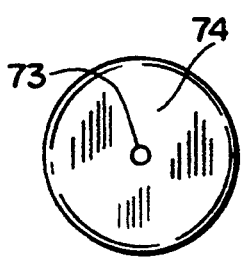
FIG. 5 is a bottom plan view illustrating the location of a diffusion port in the bottom surface.
Figure 6:
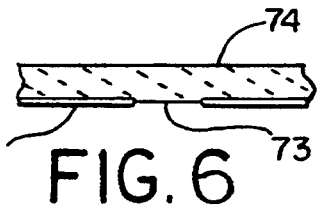
FIG. 6 is an enlarged fragmentary vertical section through such diffusion port.

Referring now additionally to FIGS. 5 and 6 it will be seen that the exterior of both the cap and the main body of the canister are externally glazed as indicated at 72 with the exception of a relatively small spot or port 73 in the center of the bottom wall 74. Since the ceramic or earthenware nature of the container or canister is somewhat porous, the copper-copper sulfate within the canister will leach out at a slow rate through the diffusion port 73 maintaining the exterior of the port moist and loaded with copper ions providing a low resistance current path from the copper core to the electrolyte 22 through the hygroscopic back-fill material 42.

The ceramic canister may take several forms as far as glazing is concerned and some of those are illustrated in FIGS. 7-13.

Figure 7:
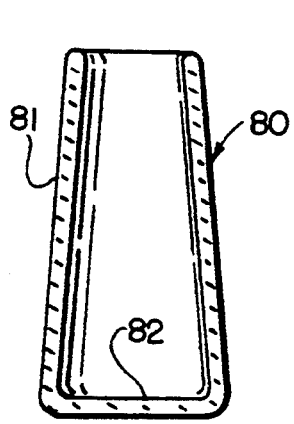
FIG. 7 is a vertical axial section through an unglazed ceramic canister which may be utilized with the present invention.

FIG. 7 illustrates a canister main body which is molded of earthenware or ceramic material indicated generally at 80 which includes the conical upright annular wall 81 and the horizontal circular bottom wall 82. The walled canister has no glazing on either surface and accordingly the porous ceramic material of the walls constitutes a diffusion path for the saturated salt solution within the canister and also a low resistance flow path for electrical current. For an unglazed ceramic vessel, a low porosity ceramic is preferred.

Figure 8:
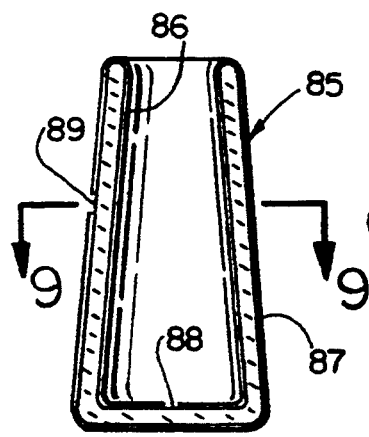
FIG. 8 is a vertical axial section of a canister which includes glazing beth inside and out with a single diffusion port being provided in the interior glazing and a single offset diffusion port provided in the exterior glazing.
Figure 9:
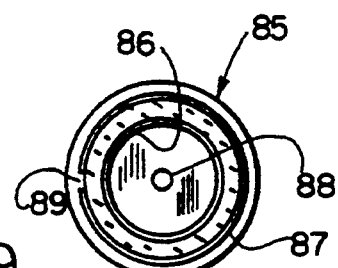
FIG. 9 is a horizontal section taken substantially through the upper diffusion port as seen from the line 9—9 of FIG. 8.

In FIGS. 8 and 9 there is an embodiment illustrated wherein the ceramic vessel 85 includes a glazing on both the interior and exterior as indicated at 86 and 87, respectively. The entire interior and exterior surface is glazed except for two relatively small ports 88 and 89. The interior port 88 is in the center of the bottom wall while the single exterior port 89 is approximately halfway up the outside or exterior glazing. Thus the leach path for the saturated salt solution as well as the low resistance current path is baffled through the porous ceramic wall of the canister.

Figure 10:
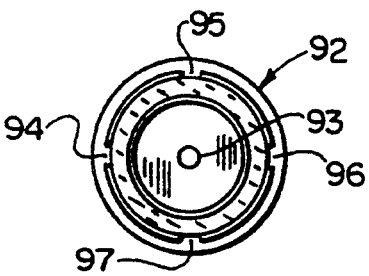
FIG. 10 is a view similar to FIG. 9 but illustrating an additional number such as four of the diffusion ports equally spaced around the exterior wall of the canister.

In FIG. 10 there is illustrated a section similar to FIG. 9 wherein the canister 92 is provided with both interior and exterior glazing as in FIG. 8 and is provided with a single bottom interior port 93, but four quadrant spaced exterior ports 94, 95, 96 and 97 which are at the same height from the bottom as in FIG. 8.

Figure 11:
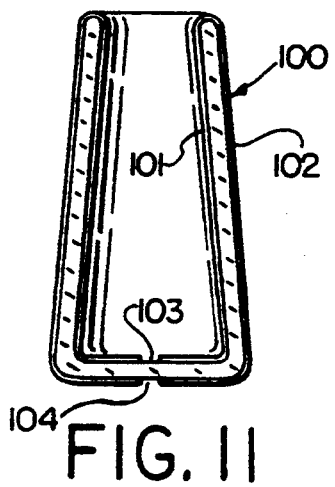
FIG. 11 is an axial section of a canister using both interior and exterior glazing with single axially aligned diffusion ports in the center of the bottom on both surface glazings.

FIG. 11 illustrates another embodiment of the present invention wherein the ceramic vessel 100 is provided with an interior and exterior glazing as indicated at 101 and 102, such glazing covering the entire internal and external surface except for two small axially aligned ports indicated at 103 and 104 in the bottom wall. Such ports define a relatively short flow path axially through the bottom both for leaching of the saturated salt to the exterior of the canister and also providing a low resistance electrical flow path.

Figure 12:
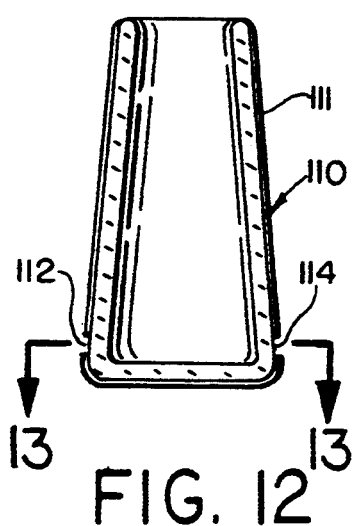
FIG. 12 illustrates a canister with only an exterior glazing and a number of exterior diffusion ports around the bottom of the canister.
Figure 13:
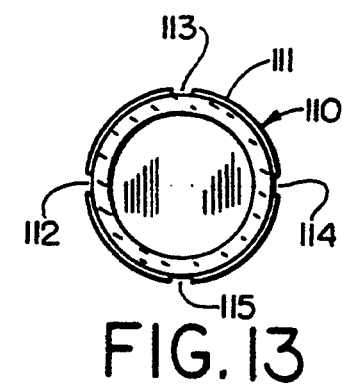
FIG. 13 is a horizontal section taken substantially on the line 13—13 of FIG. 12.

FIGS. 12 and 13 illustrate another form of ceramic vessel for the present invention, such vessel 110 including an exterior glazing 111 only, the interior of the vessel being unglazed. The exterior glazing near the bottom at the side walls is provided with four quadrant spaced ports seen at 112, 113, 114 and 115. It will thus be seen that a variety of port arrangements are useful in controlling the diffusion rate. The diffusion rate is controllable through both glazing techniques and the number, size and location of the diffusion ports.

Figure 14:
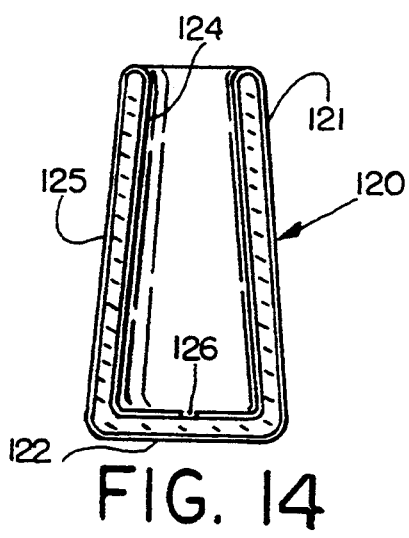
FIG. 14 is an axial section similar to FIG. 8 with only a single diffusion port on the interior glazing.

In FIG. 14 there is illustrated a ceramic vessel 120 having side walls 121 and bottom wall 122. Both the interior and exterior of the vessel are glazed as indicated at 124 and 125. The interior glazing is provided with a single bottom diffusion port seen at 126 while the exterior is provided with none. The exterior glazing has sufficient pinholes or porosity to provide the required current and leach paths.

The following experiments were conducted to determine the measurable resistance through the diffusion ports. The experiments were conducted in a 10-gallon glass aquarium which was partly filled with potable tap water having approximately 3500 ohm-cm resistivity. A copper rod was positioned at one end of the aquarium and a copper rod positioned in one of the vessels at the opposite end of the aquarium, the vessel containing a saturated copper sulfate solution. The resistance for each of several vessel configurations was measured by a Nillson Model 400 a.c. resistance meter.

In the Table I below, the vessel of Example 1 has a diffusion port on the inside bottom and no ports on the outside such as seen in FIG. 14. Example 2 has a diffusion port on the outside and the inside of the bottom wall as in FIG. 11. Example 3 has a diffusion port on the inside bottom and four side wall diffusion ports as in FIG. 10. Example 4 has a diffusion port on the inside bottom and one side wall outside port as in FIG. 8. The resistances noted in the table were measured and recorded over time intervals over a three-day period. The resistances noted are acceptable and essentially stable.

TABLE I

|  | Ex. 1 | Ex. 2 | Ex. 3 | Ex. 4 |
| --- | --- | --- | --- | --- |
| 9:50 a.m. | 43K | 13K | 17K | 19K |
| 12:10 p.m. | 43K | 12K | 16K | 18.5K |
| 1:10 p.m. | 43K | 12K | 16K | 19K |
| 2:10 p.m. | 43K | 12K | 16K | 20K |
| 3:23 p.m. | 43K | 12K | 16K | 20K |
| 4:50 p.m. | 43K | 12K | 16K | 20K |
| 1:35 p.m. | 42K | 12K | 16K | 22K |
| 2:20 p.m. | 42K | 12K | 16K | 22K |

TABLE I-continued

|  | Ex. 1 | Ex. 2 | Ex. 3 | Ex. 4 |
| --- | --- | --- | --- | --- |
| 10:40 a.m. | 42K | 12K | 16K | 27K |
| 3:15 p.m. | 41K | 13K | 15K | 26K |

The term "ceramics" includes a wide variety of clays which can be molded and fired to form earthenware, stoneware or even porcelain. Porcelain or fine stoneware has relatively low pore volume or water absorption and would be useful for the unglazed embodiment of the present invention.

Clays are the product of the weathering of feldspar, either potash feldspar, $K_2O.Al_2O_3.6SiO_2$, or soda feldspar $Na_2O.Al_2O_3.6SiO_2$, with the alkali washed away. Clay which remains at the original location is usually called a primary clay, usually white, and with a low content of iron so that it burns white. A secondary clay is one which usually has been moved by the action of water, glacier or wind to another location, having lost some of the undecomposed coarse particles of feldspar which remain in the primary clays, but now also containing various impurities such as limestone, hydrated iron oxide mud and organic materials in varying amounts. The purer deposits of the secondary clays are more plastic than china clay and are called ball clays.

A typical acceptable composition for forming the liquid clay or slip would be a clay containing quartz mixed with talc and calcium carbonate to a lesser degree and which may include additions of any or all of barium carbonate, sodium carbonate or soda ash, and sodium silicate. With the addition of water a white earthenware slip is formed which is liquid clay and which should have the consistency of quite thick cream. The slip may then be cast into a plaster mold which absorbs the water in the slip. Excess slip is drained from the mold. After the mold has set, the mold is opened and the greenware is removed from the mold. The greenware is then fired in a kiln to obtain the desired ceramic vessel and cap. For the firing of the greenware a pyrometric witness cone of approximately 03 to 06 may be used. Pyrometric cones which are heat measuring devices used when firing a kiln are well known in the art. For stoneware or porcelain a large witness cone of 6 to 10 would be employed.

As far as the glaze is concerned, a wide variety of glazes and application techniques may be employed. Glazes are glass-like thin continuous coatings usually prepared from fused silicate mixtures which are fused or bonded to the earthenware surfaces.

Glaze batches include bases, intermediates, which include amphoteric oxides, and acids. A wide variety of glazes are available commercially and they may be applied to the ceramic vessel in a wide variety of applications. Such applications may take the form of painting as with a brush, pouring, immersion or dipping, spraying, and other processes. In order to form the diffusion ports, the preferred form is to place a mask over the earthenware which prevents the glaze from bonding to the ceramic substrate. After the glazing is fired, the mask and any glazing thereover may readily be removed, or is removed by burning away the mask during the firing process. If painting is employed, the glaze is simply not applied to the selected diffusion ports. Frits which are prefused particles may also be incorporated in the glaze. In any event the cap and canister are readily fabricated by conventional clay molding, firing and glazing techniques. For more background on ceramic glazes and their application techniques reference may be had to the text CERAMIC GLAZES by Cullen W. Parmelee, third edition, published by Cahners Publishing Company of Boston, Mass.

The elements of the reference cell seen in FIG. 1 are preferably not charged with the saturated copper sulfate electrolyte until the reference cell is ready to be placed into the ground. Accordingly, the elements of the reference cell have an indefinite shelf life. At the installation site the canister is simply filled with the saturated salt solution as indicated. The lead wire and plastic tube sticking out may then simply be connected to the test station. Alternatively the canister may be shipped precharged with the diffusion ports sealed with the sealing on the exterior ports removed at installation. Such an embodiment may omit the plastic tube.

The plastic tube may contain a wick and such tube may be employed to recharge the canister from time to time through the funnel in the test station. The wicked tube may also form a salt bridge for the calibration and testing of the cell as noted above.

In any event there is provided a long life, low resistant reliable and low cost reference cell for use with cathodic protection systems.

Although the invention has been shown and described with respect to certain preferred embodiments, it is obvious that equivalent alterations and modifications will occur to others skilled in the art upon the reading and understanding of this specification. The present invention includes all such equivalent alterations and modifications, and is limited only by the scope of the following claims.

What is claimed is:

1. A reference cell for a cathodic protection system comprising a pervious ceramic canister having walls adapted to contain a saturated salt solution, an electrical lead extending into said canister, said canister being surrounded by encased hygroscopic material, the wills of said canister including a substantially impervious glaze coating except in one or more small unglazed areas, said one or more small unglazed areas forming with the wall of the canister a slow rate diffusion path for the salt solution and a low resistance current flow path.

2. A reference cell as set forth in claim 1 wherein both the interior and exterior of said canister are glazed, and at least one diffusion port in both the interior and exterior glazing.

3. A reference cell as set forth in claim 1 including a diffusion port in the bottom interior glazing of the canister.

4. A reference cell as set forth in claim 3 including at least one diffusion port in the exterior glazing spaced from the bottom.

5. A reference cell as set forth in claim 4 including four spaced diffusion ports in the exterior glazing.

6. A reference cell as set forth in claim 1 wherein said canister includes a sealed cap through which the electrical lead extends, and a plastic tube extending through said cap whereby said salt solution may be replenished, said lead and said tube further extending through said encased hygroscopic material.

7. An electrode for a cathodic protection system adapted to be placed in an electrolyte in or adjacent the structure to be protected, comprising a porous ceramic canister having walls surrounded by said electrolyte, said canister including a lead for said electrode and adapted to contain a saturated salt solution, glazing on said walls of said canister, and at least one diffusion port in said glazing, said diffusion port and said walls of said canister forming a diffusion path for leaching at a slow rate the salt solution to the exterior of the canister.

8. An electrode as set forth in claim 7 wherein both the interior and exterior of said canister are glazed.

9. An electrode as set forth in claim 8 including diffusion port in the bottom interior glazing of the canister.

10. An electrode as set forth in claim 9 including at least one diffusion port on the exterior glazing spaced from the bottom.

11. An electrode as set forth in claim 7 wherein said canister includes a sealed cap through which an electrical lead extends, and a plastic tube extending through said cap whereby said salt solution may be replenished, said lead and said tube further extending through said conductive medium.

12. An electrode as set forth in claim 11 wherein said canister is contained in a hygroscopic material.

* * * * *

UNITED STATES PATENT AND TRADEMARK OFFICE
CERTIFICATE OF CORRECTION

PATENT NO. : 5,370,783

DATED : December 6, 1994

INVENTOR(S) : Carlson, et al.

It is certified that error appears in the above-identified patent and that said Letters Patent is hereby corrected as shown below:

Column 3, line 16, change "beth" to --both--.

Column 4, line 2, change "beth" to --both--.

Column 7, line 38, change "wills" to --walls--.

Column 8, line 31, after "including", insert --a--.

Signed and Sealed this

Eleventh Day of July, 1995

Attest:

BRUCE LEHMAN

Attesting Officer     Commissioner of Patents and Trademarks